(12) United States Patent
Scalone

(10) Patent No.: US 6,620,941 B2
(45) Date of Patent: Sep. 16, 2003

(54) PROCESS FOR THE PREPARATION OF THIAZOLIDINEDIONE DERIVATIVES

(75) Inventor: Michelangelo Scalone, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/288,316

(22) Filed: Nov. 5, 2002

(65) Prior Publication Data

US 2003/0092916 A1 May 15, 2003

Related U.S. Application Data

(62) Division of application No. 09/814,907, filed on Mar. 22, 2001.

(30) Foreign Application Priority Data

Apr. 14, 2000 (EP) ............................................. 00108303

(51) Int. Cl.⁷ ...................... C07D 263/30; C07D 413/04
(52) U.S. Cl. ......................................... 548/235; 549/60
(58) Field of Search .............................. 548/235; 549/60

(56) References Cited

U.S. PATENT DOCUMENTS 6,258,832 B1    7/2001   Kuhnle et al.

FOREIGN PATENT DOCUMENTS

| DE | 1 241 428 | 6/1967 |
|---|---|---|
| DE | 2 130 296 | 2/1972 |
| EP | 177 353 | 4/1986 |
| EP | 1 078 923 | 2/2001 |
| WO | WO94/27995 | 12/1994 |
| WO | WO 96/00202 | 1/1996 |
| WO | WO 98/42691 | 10/1998 |
| WO | WO 98/42704 | 10/1998 |

OTHER PUBLICATIONS

Patwardhan et al., Synthesis, pp. 348–349 (1974).
Iwasaki et al., J. Org. Chem., vol. 56, pp. 1922–1927 (1991).
Napier et al., J. Heterocycl. Chem., vol. 7, pp. 393–394 (1970).
Malamas et al., J. Med. Chem. 43, pp. 995–1010 (2000).
L. A. Paquette, Encyclopedia of Reagents for Organic Synthesis, vol. 5, L–M, pp. 3096–3104 (1995).
Zask et al., J. Med. Chem. 33, pp. 1418–1423 (1990).
Taylor et al., Synthesis, pp. 310–311 (1971).

*Primary Examiner*—Joseph K. McKane
*Assistant Examiner*—Golam M. M. Shameem
(74) *Attorney, Agent, or Firm*—George W. Johnston; Dennis P. Tramaloni; Lyman H. Smith

(57) ABSTRACT

The present invention is concerned with a novel process for the preparation of compounds of formula I

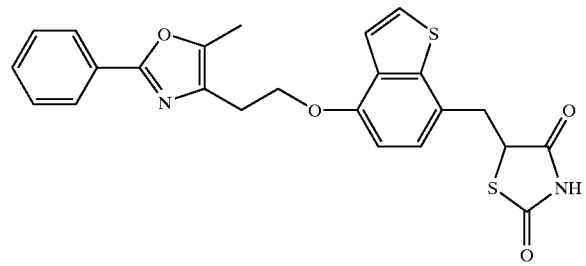

comprising bromomethylation or chloromethylation of a compound of formula II

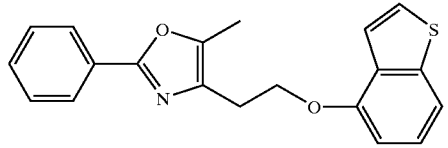

and subsequent reaction with a compound of formula IV

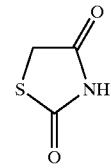

The compounds of formula I and the corresponding salts, e.g. the sodium salts, are pharmaceutically active substances.

7 Claims, No Drawings

PROCESS FOR THE PREPARATION OF THIAZOLIDINEDIONE DERIVATIVES

CROSS REFERENCE TO RELATED APPLICATION

This is a divisional of Ser. No. 09/814,907, filed Mar. 22, 2001.

BACKGROUND OF THE INVENTION

The present invention is concerned with a novel process for the preparation of thiazolidinedione derivatives, especially with the preparation of 5-{4-[2-(5-Methyl-2-phenyl-oxazol-4-yl)-ethoxy]-benzo[b]thiophen-7-ylmethyl}2,4-thiazolidinedione and its salts. 5-{4-[2-(5-Methyl-2-phenyl-oxazol-4-yl)-ethoxy]-benzo[b]thiophen-7-ylmethyl}2,4-thiazolidinedione and its salts are pharmaceutically active compounds. These compounds are known in the art and are described for example in International Patent Application WO 94/27995. They are especially useful for the prophylaxis and/or treatment of diabetes mellitus type I and II.

Methods for the preparation of 5-{4-[2-(5-Methyl-2-phenyl-oxazol-4-yl)-ethoxy]-benzo[b]thiophen-7-ylmethyl}2,4-thiazolidinedione have been described in WO 94/27995. However, these methods include a large number of individual reaction steps. Further, the methods known in the art exhibit a low yield, which makes them unsuitable for the commercial large scale production of 5-{4-[2-(5-Methyl-2-phenyl-oxazol-4-yl)-ethoxy]-benzo[b]thiophen-7-ylmethyl}2,4-thiazolidinedione.

It has surprisingly been found that using the process according to the present invention 5-{4-[2-(5-Methyl-2-phenyl-oxazol-4-yl)-ethoxy]-benzo[b]thiophen-7-ylmethyl}2,4-thiazolidinedione can be prepared with less process steps under moderate conditions with an outstanding yield.

SUMMARY OF THE INVENTION

The present invention refers to a process for the preparation of compounds of formula I

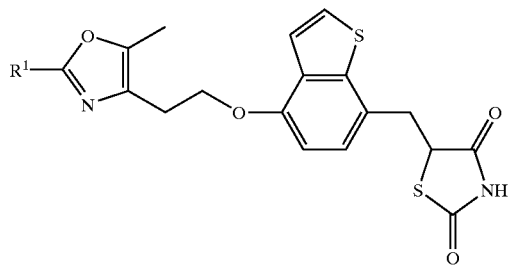

I comprising bromomethylation or chloromethylation of a compound of formula II

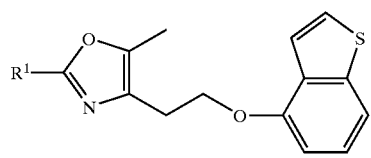

II to obtain a compound of formula III

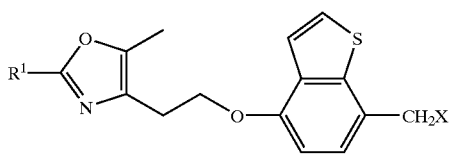

III and subsequent reaction with a compound of formula IV

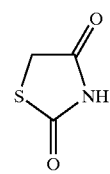

IV to yield said compounds of formula I,
wherein $R^1$ represents aryl or heteroaryl and X represents Cl or Br.

This process provides an efficient method for producing compounds of formula I. Compared to the processes known in the art, the process of the present invention exhibits a higher yield as well as a reduced number of reaction steps. Further, crude intermediate products can mostly be used in subsequent reaction steps without the need of any additional purification steps.

According to the present invention, terms "chloromethylation" and "bromomethylation" signify the introduction of a —$CH_2Cl$ or —$CH_2Br$ group respectively.

The term "mesylation" signifies the introduction of a methanesulfonyl group which can e.g. be performed by a reaction with methanesulfonylchloride.

The term "tosylation" signifies the introduction of a toluenesulfonyl group which can e.g. be performed by a reaction with toluenesulfonylchloride.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms.

The term "lower alkyl" refers to a branched or straight chain monovalent alkyl radical of one to seven carbon atoms, preferably one to four carbon atoms. This term is further exemplified by such radicals as methyl, ethyl, n-propyl, isopropyl, i-butyl, n-butyl, t-butyl and the like with methyl and ethyl being preferred.

The term "alkoxy" refers to the group alkyl-O—, the term "lower alkoxy" to the group lower-alkyl-O—.

The term "aryl" relates to the phenyl or naphthyl group which can optionally be mono-, di- or tri-substituted by alkyl, halogen, hydroxy, alkoxy, aryloxy, or aryl-alkoxy. Mono- and di-substituted phenyl or naphthyl groups are preferred.

The term "heteroaryl" refers to an aromatic 5- or 6-membered ring which can contain 1 or 2 atoms selected from nitrogen, oxygen or sulphur such as furyl, pyridyl, 1,2-, 1,3- and 1,4-diazinyl, thiophenyl, isoxazolyl, oxazolyl or imidazolyl. A heteroaryl group may have a substitution pattern as described earlier in connection with the term "aryl".

The term "halogen" refers to fluorine, chlorine, and bromine, preferably to chlorine and bromine and more preferably to bromine.

The term "pharmaceutically acceptable salt" refers to conventionally known pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases. The pharmaceutically acceptable salts are formed by taking about 1 equivalent of a compound of Formula I and contacting it with about 1 equivalent of the appropriate corresponding acid of the salt which is desired. Work-up and isolation of the resulting salt is well-known to those of ordinary skill in the art.

In detail, the present invention refers to a process for the preparation of compounds of formula I

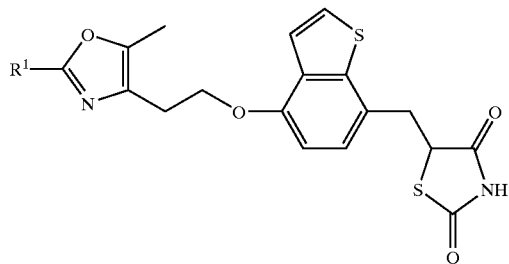

comprising bromomethylation or chloromethylation of a compound of formula II

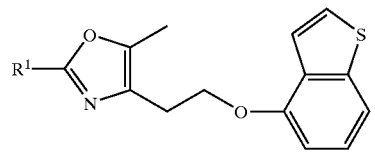

to obtain a compound of formula III

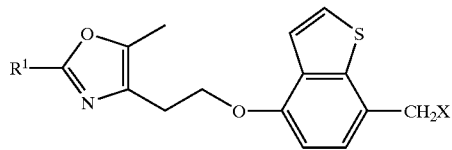

and subsequent reaction with a compound of formula IV

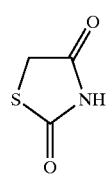

to yield said compounds of formula I,
  wherein $R^1$ represents aryl or heteroaryl and X represents Cl or Br.

In a preferred embodiment of the invention, a compound of formula II is bromomethylated. In a more preferred embodiment said bromomethylation is carried out in a solvent in the presence of HBr and formaldehyde.

Solvents for the above reaction are known to persons skilled in the art. Preferred solvents are aromatic solvents, e.g. toluene, halogenated hydrocarbons, e.g. $CH_2Cl_2$, esters, e.g. ethylacetate, ethers, e.g. dioxane, and mixtures thereof. A particularly preferred solvent is $CH_2Cl_2$.

Formaldehyde can be provided as formaline solution, trioxane or paraformaldehyde. Preferably formaldehyde is provided as trioxane in said bromomethylation.

HBr can be provided as gas or as aqueous solution. Aqueous solutions are commercially available, e.g. at concentrations of 48% or 62%. The bromomethylation can e.g. be carried out with aqueous HBr of a concentration between 30% and 69%. An aqueous solution with a HBr concentration in the range between 45% and 62% is preferred.

The bromomethylation can be carried out in a wide range of temperatures, e.g. from −20 to +40° C. Preferably, the bromomethylation is carried out at a temperature between −10 and +10° C. The atmospheric pressure during the reaction is not critical.

The reaction of a compound of formula III with a compound of formula IV may proceed by the formation of a salt of a compound of formula IV, e.g. a di-sodium salt, a di-potassium salt or a di-lithium salt, followed by reaction of that salt with the compound of formula III. A di-potassium salt of a compound of formula IV can be prepared by methods known in the art, e.g. by reacting a compound of formula IV with potassium amide in liquid ammonia or with potassium tert.-butoxyde in THF. Methods for preparing a di-sodium salt of a compound of formula IV are also known in the art, e.g. by reacting a compound of formula IV with sodium amide in liquid ammonia or with sodium tert.-butoxyde in THF.

A further preferred embodiment relates to a process as described before, wherein said reaction of a compound of formula III with a compound of formula IV comprises the formation of a di-lithium salt of a compound of formula IV. Said di-lithium salt can e.g. be obtained by reacting a compound of formula IV with lithium diisopropylamide in THF.

Preferably $R^1$ represents phenyl. In another preferred embodiment $R^1$ represents thiophen-2-yl.

If desired, compounds of formula I can be converted to a corresponding salt, preferably a pharmaceutically acceptable salt, most preferably the sodium salt. Such a conversion may be carried out under basic conditions, preferably with NaOH in THF. One embodiment of the above described process comprises the conversion of a compound of formula I to the corresponding sodium salt.

Scheme 1 summarizes one possible embodiment of the above described process and the reaction conditions for the individual reaction steps.

Scheme 1

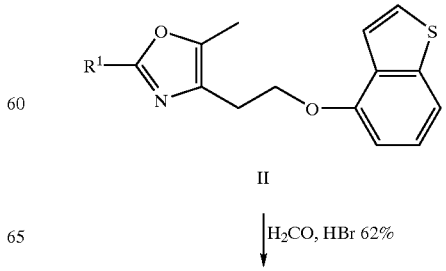

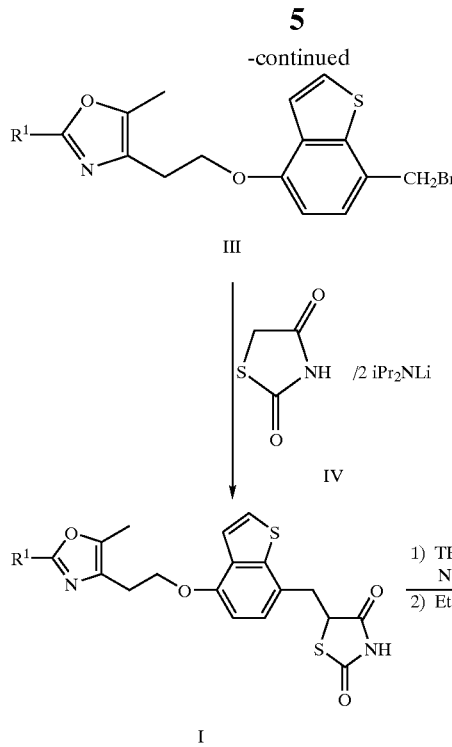

The reaction conditions for the above reaction can vary to a certain extent. Methods to perform the above described reactions and processes are known in the art or can be deduced in analogy from the examples.

The present invention also relates to processes for the preparation of starting materials for the preparation of compounds of formula I. Accordingly, the present invention relates to a process for the preparation of compounds of formula V

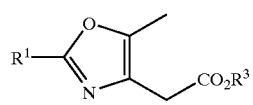

comprising bromination, preferably in γ-position, of a compound of formula VI,

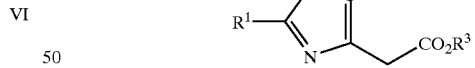

condensation of the resulting compound with an amide $R^1C(O)NH_2$ to obtain a compound of formula VII,

VII reduction of the compound of formula VII and subsequent introduction of a —$SO_2R^2$ group to yield said compounds of formula V, wherein $R^1$ represents aryl or heteroaryl, $R^2$ represents lower alkyl, aryl or trifluormethyl, and $R^3$ represents lower alkyl.

Another embodiment of the present invention relates to a process for the preparation of compounds of formula V

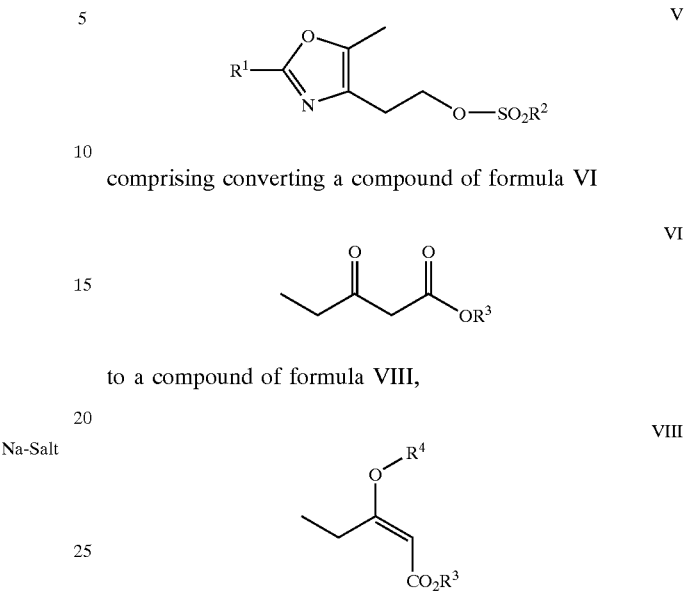

comprising converting a compound of formula VI

VI to a compound of formula VIII,

VIII and bromination, preferably in γ-position, of a compound of formula VIII to yield a compound of formula X,

X or, alternatively comprising bromination, preferably in γ-position, of a compound of formula VI and subsequent transformation to a compound of formula X, and subsequent condensation of the compound of formula X with an amide $R^1C(O)NH_2$ to obtain a compound of formula VII,

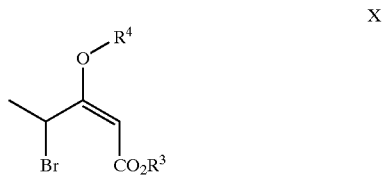

reduction of the compound of formula VII and subsequent introduction of a —$SO_2R^2$ group to yield said compound of formula V, wherein $R^1$ represents aryl or heteroaryl, $R^2$ represents lower alkyl, aryl or trifluormethyl, $R^3$ represents lower alkyl, $R^4$ represents lower alkyl, lower-alkyl-carbonyl, lower-alkoxy-carbonyl, aryl-carbonyl, $P(O)(OR^5)_2$, or $Si(R^6)_3$, each $R^5$ independently represents lower alkyl or aryl, and each $R^6$ independently represents lower alkyl or aryl.

A preferred embodiment of the invention relates to processes wherein $R^4$ represents methyl, ethyl, acetyl, benzoyl, methoxycarbonyl, ethoxycarbonyl, diethylphosphate, trimethylsilyl, triethylsilyl, or triphenylsilyl, with methyl being preferred. If $R^4$ represents $P(O)(OR^5)_2$ or $Si(R^6)_3$ the individual $R^5$ or $R^6$ substituents respectively may be different such as in ethylmethylphosphate or as in dimethylethylsilyl.

In a preferred embodiment the invention relates to processes as described above, in which $R^2$ is methyl, ethyl, trifluoromethyl, or 4-methyl-phenyl, with methyl being more preferred. Preferably, $R^3$ signifies methyl or ethyl. Preferably, $R^1$ represents phenyl and in another preferred embodiment $R^1$ represents thiophen-2-yl.

The introduction of a $-SO_2R^2$ group can e.g. be a mesylation or a tosylation.

Methods for preparing compounds of formula VIII from compounds of formula VI are known in the art, e.g. reacting a compound of formula VI with a suitable orthoformat as described in the examples or by analogous methods. See Patwardhan, et al., Synthesis 1974, 348.

In cases where $R^4$ represents lower-alkyl-carbonyl, lower-alkoxy-carbonyl, aryl-carbonyl, $P(O)(OR^5)_2$, or $Si(R^6)_3$ it may be more convenient, to carry out first the bromination, preferably in γ-position, of a compound of formula VI and then introducing the group $R^4$ prior to the subsequent condensation with an amide $R^1C(O)NH_2$. Methods for performing such reactions are described in the examples or can be deduced in analogy to the examples. Further, brominated compounds of formula VI can be reacted e.g. with:

suitable chloroformates, suitable phosphoric acid ester chlorides, suitable silyl chlorides to introduce the desired group $R^4$.

The bromination of a compound of formula VI can be carried out by methods known in the art, e.g. by reacting a compound of formula VI with bromine in the presence of p-toluenesulfonic acid monohydrate in dichloromethane.

The bromination of a compound of formula VIII can be carried out by methods known in the art, e.g. by reacting a compound of formula VIII with N-bromo-succinimide in the presence of 2,2'-azobis(2-methylpropionitrile) in carbon tetrachloride.

Condensation of brominated compounds of formula VI or VIII with an amide $R^1C(O)NH_2$ can be carried out by methods known in the art, e.g. by methods described in the examples or by analogous methods.

Scheme 2 summarises one possible embodiment of the above described processes and the reaction conditions for the individual reaction steps.

Scheme 2

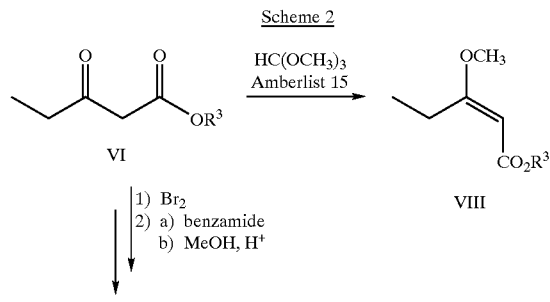

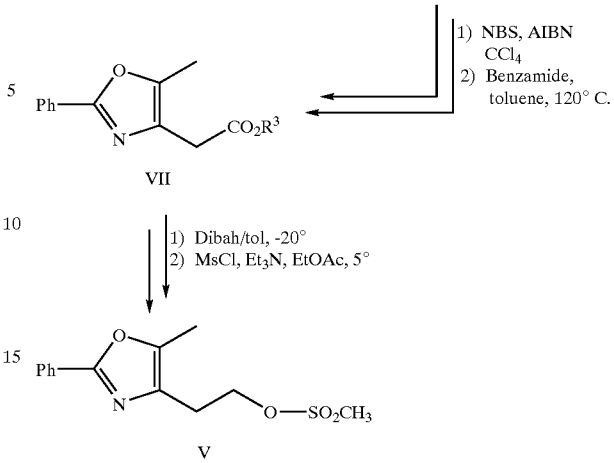

-continued

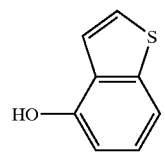

The reaction conditions for the above reaction can vary to a certain extent. Methods to perform the above described reactions and processes are known in the art or can be deduced in analogy from the examples.

Compounds of formula II can be obtained by methods known in the art, as e.g. described in WO 94/27995. One possibility to obtain compounds of formula II is by reacting compounds of formula V with compounds of formula IX

IX under basic conditions. The reaction may be performed in solvents like DMF or THF with for example sodium carbonate, potassium carbonate, sodium t-butylate, or potassium t-butylate or by phase transfer methods. Methods for the preparation of compounds of formula IX are known in the art, e.g. from Iwasaki et al., J. Org. Chem. 1991, 56, 1922.

A further embodiment of the invention comprises a process according to any of the above described processes for the preparation of 5-{4-[2-(5-Methyl-2-phenyl-oxazol-4-yl)-ethoxy]-benzo[b]thiophen-7-ylmethyl}2,4-thiazolidinedione or Sodium 5-{4-[2-(5-Methyl-2-phenyl-oxazol-4-yl)-ethoxy]-benzo[b]thiophen-7-ylmethyl}2,4-thiazolidinedionate comprising a) reacting methyl 3-oxovalerate (commercially available) with bromine to give methyl 4-bromo-3-oxovalerate, or reacting ethyl 3-oxovalerate (commercially available) with bromine to give ethyl 4-bromo-3-oxovalerate, b) reacting methyl 4-bromo-3-oxovalerate with benzamide to give methyl 2-(5-methyl-2-phenyl-4-oxazolyl)acetate, or reacting ethyl 4-bromo-3-oxovalerate with benzamide to give ethyl 2-(5-methyl-2-phenyl-4-oxazolyl)acetate, c) converting methyl 2-(5-methyl-2-phenyl-4-oxazolyl)acetate to 2-(5-methyl-2-phenyl-4-oxazolyl)ethanol, or converting ethyl 2-(5-methyl-2-phenyl-4-oxazolyl)acetate to 2-(5-methyl-2-phenyl-4-oxazolyl)ethanol, d) reacting 2-(5-methyl-2-phenyl-4-oxazolyl)ethanol with methanesulfonylchloride to give 2-(5-methyl-2-phenyl-4-oxazolyl)ethanol methansulfonyl ester, e) reacting 2-(5-Methyl-2-phenyl-4-oxazolyl)ethanol methanesulfonyl ester with 4-hydroxybenzothiophene (see Napier, et al., J. Heterocycl. Chem. 1970, 7, 393 for source) to give 4-[2-(benzo[b]thiophene-4-yloxy)-ethyl]-5-methyl-2-phenyl-oxazole, f) reacting 4-[2-(benzo[b]thiophene-4-yloxy)-ethyl]-5-methyl-2-phenyl-oxazole with formaldehyde and HBr to give 4-[2-(7-Bromomethyl-benzo[b]thiophen-4-yloxy)-ethyl]-5-methyl-2-phenyl-oxazole, g) reacting 4-[2-(7-Bromomethyl-benzo[b]thiophen-4-yloxy)-ethyl]-5-methyl-2-phenyl-oxazole with 2,4-thiazolidinedione (commercially available) to give 5-{4-[2-(5-Methyl-2-phenyl-oxazol-4-yl)-ethoxy]-benzo[b]thiophen-7-ylmethyl}2,4-thiazolidinedione, h) optionally converting 5-{4-[2-(5-Methyl-2-phenyl-oxazol-4-yl)-ethoxy]-benzo[b]thiophen-7-ylmethyl}2,4-thiazolidinedione to Sodium 5-{4-[2-(5-Methyl-2-phenyl-oxazol-4-yl)-ethoxy]-benzo[b]thiophen-7-ylmethyl}2,4-thiazolidinedionate.

A further embodiment of the invention comprises a process according to any of the above described processes for the preparation of 5-{4-[2-(5-Methyl-2-phenyl-oxazol-4-yl)-ethoxy]-benzo[b]thiophen-7-ylmethyl}2,4-thiazolidinedione or Sodium 5-{4-[2-(5-Methyl-2-phenyl-oxazol-4-yl)-ethoxy]-benzo[b]thiophen-7-ylmethyl}2,4-thiazolidinedionate comprising a) reacting methyl 3-oxovalerate with methyl orthoformate (commercially available) to give methyl (E)-3-methoxy-2-pentenoate, b) brominating methyl (E)-3-methoxy-2-pentenoate to form methyl (E)-4-bromo-3-methoxy-pent-2-enoate, c) reacting methyl (E)-4-bromo-3-methoxy-pent-2-enoate with benzamide to give methyl 2-(5-methyl-2-phenyl-4-oxazolyl)acetate, d) reducing methyl 2-(5-methyl-2-phenyl-4-oxazolyl) acetate to 2-(5-methyl-2-phenyl-4-oxazolyl)ethanol, e) reacting 2-(5-methyl-2-phenyl-4-oxazolyl)ethanol with methanesulfonylchloride to give 2-(5-methyl-2-phenyl-4-oxazolyl)ethanol methansulfonyl ester, f) reacting 2-(5-Methyl-2-phenyl-4-oxazolyl)ethanol methanesulfonyl ester with 4-hydroxybenzothiophene to give 4-[2-(benzo[b]thiophene-4-yloxy)-ethyl]-5-methyl-2-phenyl-oxazole, g) reacting 4-[2-(benzo[b]thiophene-4-yloxy)-ethyl]-5-methyl-2-phenyl-oxazole with formaldehyde and HBr to give 4-[2-(7-Bromomethyl-benzo[b]thiophen-4-yloxy)-ethyl]-5-methyl-2-phenyl-oxazole, h) reacting 4-[2-(7-Bromomethyl-benzo[b]thiophen-4-yloxy)-ethyl]-5-methyl-2-phenyl-oxazole with 2,4-thiazolidinedione to give 5-{4-[2-(5-Methyl-2-phenyl-oxazol-4-yl)-ethoxy]-benzo[b]thiophen-7-ylmethyl}2,4-thiazolidinedione, i) optionally converting 5-{4-[2-(5-Methyl-2-phenyl-oxazol-4-yl)-ethoxy]-benzo[b]thiophen-7-ylmethyl}2,4-thiazolidinedione to Sodium 5-{4-[2-(5-Methyl-2-phenyl-oxazol-4-yl)-ethoxy]-benzo[b]thiophen-7-ylmethyl}2,4-thiazolidinedionate.

The invention further comprises the use of any of the above described processes for the preparation of 5-{4-[2-(5-Methyl-2-phenyl-oxazol-4-yl)-ethoxy]-benzo[b]thiophen-7-ylmethyl}-2,4-thiazolidinedione and of 5-{4-[2-(5-Methyl-2-phenyl-oxazol-4-yl)-ethoxy]-benzo[b]thiophen-7-ylmethyl}-2,4-thiazolidinedione -Na-salt.

A further embodiment of the present invention comprises compounds of formula III

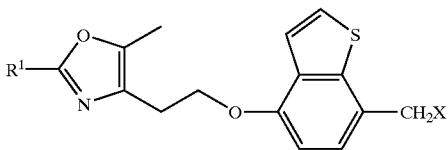

wherein $R^1$ represents aryl or heteroaryl and X represents Cl or Br. Compounds of formula III wherein X represents Br are preferred. Compounds of formula III wherein $R^1$ represents phenyl or wherein $R^1$ represents thiophen-2-yl are also preferred. Methods for the preparation of compounds of formula III are described above and are further elucidated by the examples.

The invention further relates to compounds of formula X

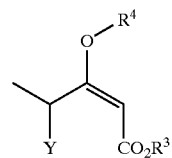

wherein
Y represents Cl or Br,
$R^3$ and $R^4$ have the significances given above
with the provisio that $R^4$ may not be methyl if Y is Br and/or $R^3$ is methyl.

Methods for preparing compounds of formula X are described above and are further elucidated by the examples. It is e.g. possible to introduce the substituent Y=Cl in analogy to the introduction of Y=Br by means of a reaction with N-chloro-succinimide.

The following examples shall illustrate preferred embodiments of the present invention but are not intended to limit the scope of the invention.

EXAMPLES

Example 1

Methyl (E)-3-Methoxy-2-pentenoate

A 250-ml 2-necked round-bottomed flask was equipped with a magnetic stirring bar, a thermometer and an argon inlet. To a mixture of 30.00 g of methyl 3-oxovalerate (0.225 mol) and 125 ml of methyl orthoformate (121.1 g, 1.12 mol) was added under stirring 7.5 g of amberlist 15. The reaction was slightly exothermal at beginning and the temperature reached 31° C. A check with Drager test tube indicated the development of carbon monoxide. The suspension was stirred at rt for 3 h and then filtered into a 500-ml 4-necked pear-shaped flask equipped with an oil bath, a thermometer, an argon inlet, a 20-cm Vigreux column with a distillation head, a vacuum pump with vacuum controller and a cold trap. The volatile components of the reaction mixture were removed by distillation at a still temperature between 37 and 48° C. and a pressure between 250 and 40 mbar. The head temperature reached max 30° C. The residue, 31.3 g Methyl (E)-3-methoxy-2-pentenoate as a yellow oil was used without purification in the next step (theor. amount 32.5 g calculated as enol ether).

Example 2

Methyl rac-(E)-4-Bromo-3-methoxy-pent-2-enoate

A 500-ml 4-necked pear-shaped flask equipped with a mechanical stirrer, a thermometer, a cooler, an argon inlet and an oil bath was charged under argon with 31.2 g of crude methyl (E)-3-methoxy-2-pentenoate (ca. 0.217 mol), 10.45 g of N-bromo succinimide (58.7 mmol), 0.47 g of 2,2'-azobis(2-methylpropionitrile) (2.86 mmol) and 100 ml of carbon tetrachloride. The resulting yellow suspension was heated for 10 min with an 80° C. oil bath to give an almost colorless suspension. Then three additional portions consisting each of 10.45 g of NBS, 0.47 g of AIBN and 35 ml of carbon tetrachloride, in total 31.35 g of N-bromo succinimide (0.176 mol), 1.41 g of 2,2'-azobis(2-methylpropionitrile) (8.59 mmol) and 105 ml of carbon tetrachloride were added in 5 min time intervals at the same temperature. 20 min after the last addition of reagents (total reaction time was 45 min) the oil bath was removed and the reaction mixture cooled under stirring with an ice bath for ca. 30 min. The suspension was filtered with suction and the filter cake washed with a total of 90 ml of carbon tetrachloride. The filtrate was rotary evaporated to dryness (50° C., 10 mbar) to give 49.7 g of crude methyl rac-(E)-4-bromo-3-methoxy-pent-2-enoate (theor. amount 48.4 g) as an orange oil. This material was used without purification in the next step.

Example 3

Methyl 2-(5-Methyl-2-phenyl-4-oxazolyl)acetate

A 200-ml 4-necked flask equipped with a mechanical stirrer, a thermometer, a distillation head, a vacuum controller, an argon inlet and an oil bath was charged with 24.7 g of crude methyl rac-(E)-4-bromo-3-methoxy-pent-2-enoate (ca. 0.107 mol), 19.91 g of benzamide (0.161 mol) and 57 ml of toluene. The orange suspension was stirred and heated with an oil bath at 120° C. At a still temperature of 111° C. low boiling componentes started to distill. The head temperature reached 103° C. after ca. 1 h and was 65° C. after 6 h. After 9 h the oil bath was removed and the reaction mixture stirred over night at rt. Thereafter the toluene was removed at 60° C. bath temperature and a pressure between 300 and 70 mbar. After cooling to rt, 80 ml of methanol and 0.60 g of p-toluenesulfonic acid monohydrate were added and the brown solution stirred at reflux (ca. 73° C.) for 2 h. Subsequently 2.5 g of charcoal and 50 ml of methanol were added, the mixture was stirred for 30 min, filtered with suction through Dicalite Speedex and rotary evaporated to dryness (50° C., 8 mbar, 30 min). The orange semi-solid residue was treated under argon with 250 ml of toluene and 55 ml of sat. aqueous sodium bicarbonate solution. The resulting suspension was stirred in an ice bath for 0.5 h, the precipitated benzamide was filtered off with suction and the filter cake was washed three times with 50 ml portions, a total of 150 ml of ice cold toluene and with little water. The combined aqueous phases (pH=8)were extracted in a separatory funnel with 80 ml of toluene. Thereafter the combined organic phases were washed twice with 50 ml, a total of 100 ml of deionized water, dried ($Na_2SO_4$) and rotary evaporated (50° C., 10 mbar, 1 h) to give 21.8 g of crude Methyl 2-(5-methyl-2-phenyl-4-oxazolyl)acetate (theor. amount 24.7 g) as a red-brown oil, which can be used without purification in subsequent steps.

Example 4

Methyl 4-Bromo-3-oxovalerate

A 200-ml 4-necked round-bottomed flask equipped with a mechanical stirrer, a thermometer, an argon inlet, a 50-ml dropping funnel and a reflux condenser connected to an absorption trap containing a 1 M NaOH solution was purged by three cycles of vacuum (ca. 0.5 mbar)/argon and charged with a solution of 33.20 g of methyl 3-oxovalerate (0.250 mol) and 0.167 g of p-toluenesulfonic acid monohydrate in 45 ml of dichloromethane. A solution of 13.5 ml of bromine (41.8 g, 0.262 mol) in 25 ml of dichloromethane was added dropwise within 30 min at 20–25° C. The reaction was slightly exothermic at the beginning and the temperature was controlled with occasional use of an ice bath. Hydrogen bromide that was formed during the reaction was carried into the NaOH-trap by a slow argon flow. The light yellow solution was heated to 30–35° C. and stirred at this temperature for 1.5 h. The excess of HBr still dissolved in the solution was carried out by bubbling argon through it for 2 h. Final rotary evaporation to dryness of the solution (50° C., 8 mbar, 1 h) afforded 54.31 g of crude Methyl 4-bromo-3-oxovalerate (theor. amount 52.26 g) as an orange-brown liquid, which was used without purification in the next step.

Example 5

Methyl 2-(5-Methyl-2-phenyl-4-oxazolyl)acetate

A 500-ml 4-necked flask equipped with a mechanical stirrer, a thermometer, a Claisen head with a condenser and a receiver connected to a cold trap and a vacuum controller was charged with 52.26 g of crude methyl 4-bromo-3-oxovalerate (ca. 0.250 mol) and 46.5 g of benzamide. A vacuum of 400 mbar was applied and the suspension was stirred at 90° C. for 18 h. After ca. 3 h the suspension had become a clear orange oil. After cooling to rt 300 ml of methanol and 1.0 g of p-toluenesulfonic acid monohydrate were added and the brown solution was stirred at reflux (ca. 73° C.) for 1 h. After this time 50 ml of methanol were distilled off, 50 ml of methanol were added and the mixture was heated at reflux for additional 30 min. After cooling and rotary evaporation (50° C., 8 mbar, 30 min), the residue was treated under argon with 150 ml of toluene and 125 ml of sat. aqueous sodium bicarbonate solution. The resulting suspension was stirred in an ice bath for 1 h, the precipitated benzamide was filtered off with suction and the filter cake was washed twice with a small amount of ice-cold toluene and water. The combined aqueous phases were extracted in a separatory funnel with 100 ml of toluene. Thereafter the combined organic phases were washed twice with 30 ml, a total of 60 ml of deionized water, dried ($Na_2SO_4$) and rotary evaporated (50° C., 8 mbar, 1 h) to give 49.22 g of crude Methyl 2-(5-methyl-2-phenyl-4-oxazolyl)acetate (theor. amount 57.81 g) as a yellow oil, which was used without purification in the next step.

Example 6

2-(5-Methyl-2-phenyl-4-oxazolyl)ethanol

A 750-ml 4-necked flask equipped with a mechanical stirrer, a thermometer, a dropping funnel and an argon inlet, cooled with a $CO_2$/acetone bath, was charged with a solution of 49.15 g of crude methyl 2-(5-methyl-2-phenyl-4-oxazolyl)acetate (ca. 0.16 mol) and 90 ml of toluene and stirred. 400 ml of diisobutyl aluminiumhydride 1.2 M in toluene were added under argon at ca. −20 to −25° C. during 60 min. After additional 15 min a solution of 191 g of citric acid monohydrate in 400 ml of deionized water was added with cooling during 30 min, so that the temperature did not exceed 5–10° C. The aqueous phase of the clear biphasic mixture was extracted with 200 ml of toluene. The combined organic phases were washed twice with 40 ml, a total of 80 ml of deionized water, twice with 40 ml, a total of 80 ml of brine and dried ($Na_2SO_4$). Rotary evaporation (50° C., 8 mbar, 1 h) afforded 38.5 g of crude 2-(5-Methyl-2-phenyl- 4-oxazolyl)ethanol (theor. amount 32.4 g) which was used in the next step without further purification.

Example 7

2-(5-Methyl-2-phenyl-4-oxazolyl)ethanol Methanesulfonyl Ester

A 750-ml 4-necked flask equipped with a mechanical stirrer, a thermometer, a dropping funnel and an argon inlet was charged with a solution of 34.60 g of crude 2-(5-methyl-2-phenyl-4-oxazolyl)ethanol (ca. 0.11 mol) in 300 ml of ethyl acetate and 28.6 ml of triethylamine (204 mmol) and stirred. 12.7 ml of mesyl chloride were added under argon with a syringe at ca. 5° C. during 10 min. The temperature was kept below 10–15° C. with the aid of an ice bath. A thick suspension formed rapidly. After removal of the ice bath and additional stirring for 30 min the suspension was filtered with suction through a fritted glass filter (G3) and the filter cake was washed three times with 75 ml, a total of 225 ml of ethyl acetate. The combined organic filtrates were washed twice with 80 ml, a total of 160 ml of deionized water and twice with 80 ml, a total of 160 ml of brine. The combined aqueous phases (pH=6) were extracted with 100 ml of ethyl acetate. The combined organic phases were dried ($Na_2SO_4$) and rotary evaporated to dryness (45° C., 8 mbar, 1 h). The orange solid residue (45.67g) was dissolved at 77° C. bath temperature in 150 ml of ethanol, then the bath was removed and the crystallization started spontaneously within a few minutes. The thick crystalline mass was stirred at rt for 1 h, kept in the freezer (−20° C.) for 60 h and finally filtered with suction. The filter cake was washed twice with 75 ml, a total of 150 ml of ethanol (cooled to −20° C.) and dried at the rotovapor (50° C., 10 mbar, 1 h) to constant weight to afford 29.65 g of 2-(5-Methyl-2-phenyl-4-oxazolyl)ethanol methanesulfonyl ester as light beige crystals with a m.p. of 87–88° C. Rotary evaporation of the mother liquors and drying as above left 15.55 g of a red-brown residue, which contained ca. 2.0 g of 2-(5-Methyl-2-phenyl-4-oxazolyl) ethanol methanesulfonyl ester. The overall yield relative to the starting amount of methyl 4-bromo-3-oxovalerate was 41%.

Example 8

Synthesis of 2-(5-Methyl-2-phenyl-4-oxazolyl) ethanol Methanesulfonyl Ester Starting from ethyl 3-oxovalerate The synthesis was done in an analogous manner as described in the previous examples. Bromination of 36.41 g (0.250 mol) of ethyl 3-oxovalerate afforded 57.28 g of crude ethyl 4-bromo-3-oxovalerate which was condensed with benzamide. The resulting 53.20 g of crude ethyl ester (brown oil) were reduced with DIBAH to give 38.5 g of 2-(5-Methyl-2-phenyl-4-oxazolyl)ethanol (brown oil). Mesylation of 2-(5-Methyl-2-phenyl-4-oxazolyl)ethanol afforded after crystallization 29.78 g of 2-(5-Methyl-2-phenyl-4-oxazolyl)ethanol methanesulfonyl ester with a m.p. of 86–88° C. A second fraction of 1.7 g of 2-(5-Methyl-2-phenyl-4-oxazolyl)ethanol methanesulfonyl ester was obtained from the mother liquors. The overall yield of 2-(5-Methyl-2-phenyl-4-oxazolyl)ethanol methanesulfonyl ester relative to ethyl 3-oxovalerate was 44%.

Example 9

4-[2-(Benzo[b]thiophene-4-yloxy)-ethyl]-5-methyl-2-phenyl-oxazole 218 g (1.45 mol) of 4-hydroxy-benzothiophene and 511 g (1.82 mol) 2-(5-Methyl-2-phenyl-4-oxazolyl)ethanol methanesulfonyl ester were dissolved in 5.4 l of DMF, followed by addition of 555 g (4,02 mol) of potassium carbonate (dry). The reaction mixture was stirred at 100 to 105 ° C. for 6 to 8 hours. The resulting suspension was cooled to 5° C. and 7 l water was added. The suspension was stirred at 5 ° C. for 30 minutes. The precipitate was filtered with suction and washed with 550 ml of DMF/water (1:1) and 1,1 l water. The precipitate was stirred at 0 to 5° C. in 1 l of MEK (methylethylketone) for 30 minutes. Then the precipitate was filtered with suction and dried at 50° C., affording 365 g (=75%) 4-[2-(benzo[b]thiophene-4-yloxy)-ethyl]-5-methyl-2-phenyl-oxazole.with a m.p.126° C./129–131° C.

Example 10

4-[2-(7-Bromomethyl-benzo[b]thiophen-4-yloxy)-ethyl]-5-methyl-2-phenyl-oxazole A 500-ml 4-necked jacketed reactor equipped with a mechanical stirrer, a thermometer, a 50-ml dropping funnel, an argon inlet, a PT100 temperature sensor and a thermostat was charged with 33.54 g of 4-[2-(Benzo[b]thiophene-4-yloxy)-ethyl]-5-methyl-2-phenyl-oxazole (0.100 mol) and 400 ml of dichloromethane. After cooling the solution to 0° C., 30.3 ml of hydrobromic acid 62% (0.400 mol) were added dropwise within 9 min at a temperature of 0°–4° C. To the yellow biphasic mixture a solution of 3.30 g of trioxane (0.110 mol) in 40 ml of dichloromethane was added at 0–1° C. After 3 h 15.1 ml of hydrobromic acid 62% (0.200 mol) were added within 7 min at 0–1° C. After 4 h additional 15.1 ml of hydrobromic acid 62% (0.200 mol) were added and the mixture was stirred over night at 0° C. After a total of 24 h the colorless bottom HBr-phase was removed through the bottom valve and extracted with 100 ml of dichloromethane. To the combined organic phases in the reactor 300 ml of sat. aqueous sodium bicarbonate solution were added at ca. 0° within 30 min. The resulting biphasic mixture was stirred for 5 min and the aqueous phase was extracted twice with 100 ml, a total of 200 ml of dichloromethane. The combined organic phases were dried ($Na_2SO_4$), rotary evaporated (45°, 600 mbar) and shortly dried (45° C., 20 mbar, 15 min). The resulting light brown residue was suspended in 200 ml of acetone and the suspension stirred for 1 h at reflux, 1 h at rt and 1 h in an ice bath. The crystals were filtered off with suction, washed with 50 ml of cold (−20° C.) acetone and dried to constant weight at 55° C. and 10 mbar for 4 h, affording 24.88 g of 4-[2-(7-Bromomethyl-benzo[b] thiophen-4-yloxy)-ethyl]-5-methyl-2-phenyl-oxazole as off-white crystals with m.p of 143–144° C.

Example 11

5-{4-[2-(5-Methyl-2-phenyl-oxazol-4-yl)-ethoxy]-benzo[b]thiophen-7-ylmethy}2,4-thiazolidinedione A 1500-ml 4-necked flask was equipped with a mechanical stirrer, a thermometer, a dropping funnel and an argon inlet. To a solution of 11.71 g of 2,4-thiazolidinedione (0.100 mol) in 600 ml of tetrahydrofurane 100 ml of lithium diisopropylamide 2.0 M in THF/heptane/ethylbenzene (0.200 mol) were added dropwise within 30 min at a temperature between −2° and 0° C. The light brown suspension was stirred at −2° C. for 10 min and then a solution of 17.14 g of 4-[2-(7-Bromomethyl-benzo[b]thiophen-4-yloxy)-ethyl]-5-methyl-2-phenyl-oxazole in 250 ml of tetrahydrofuran was added dropwise at −20° C. within 1 h 15 min. After stirring for 30 min, 160 ml of deionized water were added to the yellow suspension within 12 min at −20°–−4° C. The resulting yellow emulsion was stirred for 70 min at 2° C., transferred to a rotary evaporator with aid of a total of 75 ml of tetrahydrofurane and of a total of 75 ml of deionized water. The largest part of organic solvents was removed (45° C., 250 mbar) and the residue (237 g of turbid aqueous phase) was treated with 200 ml of t-butyl methylether. The resulting yellow thick suspension was stirred in an ice bath for 1 h, then 22 ml of hydrochloric acid 25% (170 mmol) were added dropwise and the resulting beige suspension was stirred for 15 min in an ice bath and filtered with suction. The filter cake was washed three times with 10 ml, a total of 30 ml of cold (2° C.) deionized water, three times with 10 ml, a total of 30 ml of t-butyl methylether and dried to constant weight (80° C., 0.15 mbar, 17 h), affording 15.97 g (85.9%) of 5-{4-[2-(5-Methyl-2-phenyl-oxazol-4-yl)-ethoxy]-benzo[b]thiophen-7-ylmethyl}2,4-thiazolidinedione as off-white crystals with a m.p. of 195.5–197° C.

Example 12

Sodium 5-{4-[2-(5-Methyl-2-phenyl-oxazol-4-yl)-ethoxy]-benzo[b]thiophen-7-ylmethyl}2,4-thiazolidinedionate A 250-ml round-bottomed flask equipped with a magnetic stirring bar, a condenser and an argon inlet was charged with 11.61 g of 5-{4-[2-(5-Methyl-2-phenyl-oxazol-4-yl)-ethoxy]-benzo[b]thiophen-7-ylmethyl}2,4-thiazolidinedione (25 mmol) and 175 ml of tetrahydrofuran and the mixture was heated to reflux (T$_{bath}$ 75° C.). To the resulting yellowish slightly turbid solution were added within 2 min a solution of 1.030 g of sodium hydroxide in 12 ml of deionized water. After removal of the oil bath, the resulting yellowish solution was cooled to room temperature with aid of a water bath and filtered with suction through a D4 sintered glass filter into a 4-necked flask equipped with a mechanical stirrer, a thermometer, a Claisen distillation head, a thermometer and an argon inlet. The flask and the filter were washed with a total of 175 ml of tetrahydrofuran and the resulting cloudy solution was heated with an oil bath (75° C.) to distill off the tetrahydrofuran. During all the distillation (ca. 3 h) a slow argon flow was sent through the apparatus. The suspension was heated to reflux for 1 h, then cooled to rt and finally stirred for 2 h in an ice bath. The precipitate was filtered with suction and the filter cake was washed with three times 15 ml, a total of 45 ml of cold (−20° C.) tetrahydrofuran and dried to constant weight (50° C., 10 mbar, 17 h) to afford 10.65 g (87%) of Sodium 5-{4-[2-(5-Methyl-2-phenyl-oxazol-4-yl)-ethoxy]-benzo[b]thiophen-7-ylmethyl}2,4-thiazolidinedionate as white crystals with a mp of >250° C.

Example 13

Methyl 3-acetoxy-4-bromo-2-butenoate

A solution of 10.45 g of methyl 4-bromovalerate (50 mmol) in 50 ml of tert.-butyl methylether was treated with 14.5 ml of pyridine (180 mmol), 623 mg of 4-dimethylamino pyridine (5 mmol) and 17.0 ml of acetic anhydride (180 mmol) for 1.5 h at room temperature. The resulting suspension was filtered through celite, evaporated to dryness and distilled at 0.8 mbar/110° C., to give 7.1 g of a colorless oil, which consisted of methyl 3-acetoxy-4-bromo-2-butenoate with more than 70% purity as an E/Z mixture.

Example 14

Methyl 2-(5-Methyl-2-phenyl-4-oxazolyl)acetate from Methyl 3-acetoxy-4-bromo-2-butenoate A solution of 5.0 g of methyl 3-acetoxy-4-bromo-2-butenoate (19.9 mmol) in 40 ml of toluene was treated with 3.69 g of benzamide (29.9 mmol) in an oil bath at 120° C. The formed low boilings were distilled off continuously during 17 h. The brown solution was treated with 40 ml of methanol and 1 g of charcoal during 2 h, then filtered and evaporated to dryness to give 6.0 g of a brown oil, which contained 33% of methyl 2-(5-methyl-2-phenyl-4-oxazolyl) acetate according to HPLC analysis, which corresponds to 43% chemical yield.

Example 15

4-[2-(7-Chloromethyl-benzo[b]thiophen-4-yloxy)-ethyl]-5-methyl-2-phenyl-oxazole

A solution of 335 mg of 4-[2-(Benzo[b]thiophene-4-yloxy)-ethyl]-5-methyl-2-phenyl-oxazole (1 mmol) and 110 mg of Trioxane (3.6 mmol) in 15 ml dichloromethane was treated with 2 ml of 37% HCl solution and saturated for 10 min with HCl gas and reacted at 2° C. for 23 h. The resulting mixture was extracted wich 10% sodium carbonate solution and water and evaporated to dryness. Digestion with tert. butyl methylether at room temperature left a light brown residue (0.11 g) consisting of 4-[2-(7-Chloromethyl-benzo[b]thiophen-4-yloxy)-ethyl]-5-methyl-2-phenyl-oxazole with a m.p. of 144–145° C.

What is claimed is:

1. A process for the preparation of a compound of formula V,

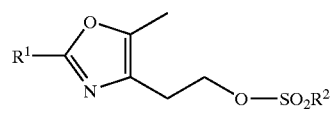

V wherein R$^1$ is aryl or heteroaryl, and

R$^2$ is lower alkyl, aryl or trifluoromethyl;

comprising converting a compound of formula VI

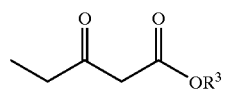

VI wherein R$^3$ is lower alkyl, to a compound of formula VIII,

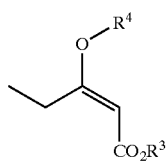

VIII wherein $R^3$ is as above,
and $R^4$ is lower alkyl, lower-alkyl-carbonyl, lower-alkoxy-carbonyl, aryl-carbonyl, $P(O)(OR^5)_2$, or $Si(R^6)_3$, wherein
  each $R^5$ independently represents lower alkyl or aryl, and
  each $R^6$ independently represents lower alkyl or aryl;
brominating the compound of formula VIII to yield a compound of formula X,

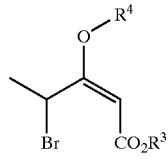

X wherein $R^3$ and $R^4$ are as above, subsequently condensing of the compound of formula X with an amide $R^1C(O)NH_2$, wherein $R^1$ is as above, to obtain a compound of formula VII,

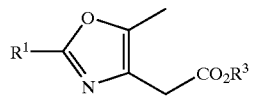

VII wherein $R^1$ and $R^3$ are as above,
reducing the compound of formula VII to convert the ester group to a corresponding alcohol, and
subsequently introducing a $-SO_2R^2$ group, wherein $R^2$ is as above, to yield said compounds of formula V.

2. A process according to claim 1, wherein $R^4$ is methyl.

3. A process according to claim 1, wherein $R^3$ is methyl or ethyl.

4. A process according to claim 1, wherein $R^2$ is methyl, ethyl, trifluoromethyl or 4-methyl-phenyl.

5. A process according to claim 4, wherein $R^2$ is methyl.

6. A process according to claim 1, wherein $R^1$ is phenyl.

7. A process according to claim 1, wherein $R^1$ is thiophen-2-yl.

* * * * *